United States Patent
Wu et al.

(10) Patent No.: US 7,724,865 B2
(45) Date of Patent: May 25, 2010

(54) SYSTEM AND METHOD OF OPTIMIZING A MONOCHROMATIC REPRESENTATION OF BASIS MATERIAL DECOMPOSED CT IMAGES

(75) Inventors: Xiaoye Wu, Rexford, NY (US); John Eric Tkaczyk, Delanson, NY (US); James W. LeBlanc, Niskayuna, NY (US)

(73) Assignee: General Electric Company, Niskayuna, NY (US)

( * ) Notice: Subject to any disclaimer, the term of this patent is extended or adjusted under 35 U.S.C. 154(b) by 287 days.

(21) Appl. No.: 11/843,031

(22) Filed: Aug. 22, 2007

(65) Prior Publication Data

US 2009/0052612 A1 Feb. 26, 2009

(51) Int. Cl.
*A61B 6/00* (2006.01)

(52) U.S. Cl. .............................. 378/5; 378/4; 378/98.9; 378/98.12

(58) Field of Classification Search ............... 378/4, 378/5, 98.9, 98.11, 98.12
See application file for complete search history.

(56) References Cited

U.S. PATENT DOCUMENTS

| | | | | |
|---|---|---|---|---|
| 3,848,130 A | * | 11/1974 | Macovski | 378/98.9 |
| 4,029,963 A | * | 6/1977 | Alvarez et al. | 378/5 |
| 4,445,226 A | * | 4/1984 | Brody | 378/98.9 |
| 4,463,375 A | * | 7/1984 | Macovski | 378/98.12 |
| 5,115,394 A | * | 5/1992 | Walters | 382/131 |
| 5,155,365 A | * | 10/1992 | Cann et al. | 250/363.02 |
| 6,226,352 B1 | * | 5/2001 | Salb | 378/98.9 |
| 6,614,874 B2 | * | 9/2003 | Avinash | 378/62 |
| 6,683,934 B1 | * | 1/2004 | Zhao et al. | 378/9 |
| 6,898,263 B2 | * | 5/2005 | Avinash et al. | 378/4 |
| 6,904,118 B2 | * | 6/2005 | Wu et al. | 378/5 |
| 2007/0076842 A1 | * | 4/2007 | Tkaczyk et al. | 378/5 |

OTHER PUBLICATIONS

Alvarez et al., Energy-selective Reconstructions in X-ray Computerized Tomography, Phys Med Biol, 1976, vol. 21, No. 5, pp. 733-744.*
Wang et al., Optimization of Energy Window Widths in Basis Material Decomposition Using a Multi-window Photon Counting X-ray Detector, IEEE Nuclear Symposium Conference Record, 2007, pp. 3826-3829.*

* cited by examiner

*Primary Examiner*—Edward J Glick
*Assistant Examiner*—Alexander H Taningco
(74) *Attorney, Agent, or Firm*—Scott J. Asmus

(57) ABSTRACT

A system and method of a diagnostic imaging system includes a high frequency electromagnetic energy source that emits a beam of high frequency electromagnetic energy toward an object to be imaged, a detector that receives high frequency electromagnetic energy emitted by the high frequency electromagnetic energy source and attenuated by the object, a data acquisition system (DAS) operably connected to the detector, and a computer operably connected to the DAS. The computer is programmed to obtain CT scan data with two or more incident energy spectra, decompose the obtained CT scan data into projection CT data of two or more basis materials, reconstruct linearly weighted projections of the two or more basis materials, determine an optimized energy for the two or more basis materials within a region-of-interest (ROI), and form a monochromatic image of the projection CT data at the optimized energy using the two or more basis material projections.

18 Claims, 6 Drawing Sheets

SYSTEM AND METHOD OF OPTIMIZING A MONOCHROMATIC REPRESENTATION OF BASIS MATERIAL DECOMPOSED CT IMAGES

BACKGROUND OF THE INVENTION

The present invention relates generally to diagnostic imaging and, more particularly, to a system and method of basis material decomposition and representation of diagnostic imaging data at a virtual energy having minimized monochromatic noise or maximized contrast to noise ratio.

Diagnostic devices comprise x-ray systems, magnetic resonance (MR) systems, ultrasound systems, computed tomography (CT) systems, positron emission tomography (PET) systems, ultrasound, nuclear medicine, and other types of imaging systems. Typically, in CT imaging systems, an x-ray source emits a fan-shaped beam toward a subject or object, such as a patient or a piece of luggage. Hereinafter, the terms "subject" and "object" shall include anything capable of being imaged. The beam, after being attenuated by the subject, impinges upon an array of radiation detectors. The intensity of the attenuated beam radiation received at the detector array is typically dependent upon the attenuation of the x-ray beam by the subject. Each detector element of the detector array produces a separate electrical signal indicative of the attenuated beam received by each detector element. The electrical signals are transmitted to a data processing system for analysis which ultimately produces an image.

Generally, the x-ray source and the detector array are rotated about the gantry opening within an imaging plane and around the subject. X-ray sources typically include x-ray tubes, which emit the x-ray beam at a focal point. X-ray detectors typically include a collimator for collimating x-ray beams received at the detector, a scintillator for converting x-rays to light energy adjacent the collimator, and photodiodes for receiving the light energy from the adjacent scintillator and producing electrical signals therefrom.

Typically, each scintillator of a scintillator array converts x-rays to light energy. Each scintillator discharges light energy to a photodiode adjacent thereto. Each photodiode detects the light energy and generates a corresponding electrical signal. The outputs of the photodiodes are then transmitted to the data processing system for image reconstruction.

A CT imaging system may include an energy discriminating (ED), multi energy (ME), and/or dual energy (DE) CT imaging system that may be referred to as an EDCT, MECT, and/or DE-CT imaging system. Such systems may use a direct conversion detector material in lieu of a scintillator. The EDCT, MECT, and/or DE-CT imaging system in an example is configured to be responsive to different x-ray spectra. For example, a conventional third generation CT system may acquire projections sequentially at different peak kilovoltage (kVp) levels, which changes the peak and spectrum of energy of the incident photons comprising the emitted x-ray beams. Two scans are acquired—either (1) back-to-back sequentially in time where the scans require two rotations around the subject, or (2) interleaved as a function of the rotation angle requiring one rotation around the subject, in which the tube operates at, for instance, 80 kVp and 160 kVp potentials. Special filters may be placed between the x-ray source and the detector such that different detector rows collect projections of different x-ray energy spectra. The special filters that shape the x-ray spectrum may be used for two scans that are acquired either back to back or interleaved. Energy sensitive detectors may be used such that each x-ray photon reaching the detector is recorded with its photon energy.

Techniques to obtain the measurements comprise: (1) scan with two distinctive energy spectra, and (2) detect photon energy according to energy deposition in the detector. EDCT/MECT/DE-CT provides energy discrimination and material characterization. For example, in the absence of object scatter, the system derives the behavior at a different energy based on the signal from two regions of photon energy in the spectrum: the low-energy and the high-energy portions of the incident x-ray spectrum. In a given energy region of medical CT, two physical processes dominate the x-ray attenuation: (1) Compton scatter and the (2) photoelectric effect. The detected signals from two energy regions provide sufficient information to resolve the energy dependence of the material being imaged. Furthermore, detected signals from the two energy regions provide sufficient information to determine the relative composition of an object composed of two hypothetical materials.

A conventional basis material decomposition (BMD) algorithm is based on the concept that, in an energy region for medical CT, the x-ray attenuation of any given material can be represented by a proper density mix of two materials with distinct x-ray attenuation properties, referred to as the basis materials. The BMD algorithm computes two CT images that represent the equivalent density of one of the basis materials based on the measured projections at high and low x-ray photon energy spectra, respectively. Because of the strong energy dependence of x-ray attenuation coefficients and the polychromatic nature of the x-ray spectrum, conventional CT images typically contain beam hardening artifacts, except in a given material—typically water, that the system is typically calibrated with. However, since a material density is independent of x-ray photon energy, beam-hardening artifacts can be greatly reduced or eliminated. The drawback is that the density images often have increased noise due to the BMD process. By linearly combining the two density images, a monochromatic image representation can be formed, resulting in a reduced noise level if proper weighting is used.

Therefore, it would be desirable to have a system and method that presents diagnostic imaging data having minimized noise or maximized contrast to noise ratio in the computed monochromatic images.

BRIEF DESCRIPTION OF THE INVENTION

The present invention is directed to a system and method for providing monochromatic images having minimized noise or maximized contrast to noise ratio.

An energy discriminating CT detector capable of photon counting is disclosed. The CT detector includes a semi-conductor layer having a plurality of pixelated anodes attached thereto. The CT detector supports not only x-ray photon counting, but energy measurement or tagging as well. As a result, the present invention supports the acquisition of both anatomical detail as well as tissue characterization information. In this regard, the energy discriminatory information or data may be used to reduce the effects of beam hardening and the like. Furthermore, these detectors support the acquisition of tissue discriminatory data and therefore provide diagnostic information that is indicative of disease or other pathologies. This detector can also be used to detect, measure, and characterize materials that may be injected into the subject such as contrast agents and other specialized materials by the use of optimal energy weighting to boost the contrast of iodine and calcium (and other high atomic or materials). Contrast agents can, for example, include iodine that is injected into the blood stream for better visualization.

According to an aspect of the present invention, a diagnostic imaging system includes a high frequency electromagnetic energy source that emits a beam of high frequency electromagnetic energy toward an object to be imaged, a detector that receives high frequency electromagnetic energy emitted by the high frequency electromagnetic energy source and attenuated by the object, a data acquisition system (DAS) operably connected to the detector, and a computer operably connected to the DAS. The computer is programmed to obtain CT scan data with two or more incident energy spectra, decompose the obtained CT scan data into projection CT data of two or more basis materials, reconstruct linearly weighted projections of the two or more basis materials, determine an optimized energy for the two or more basis materials within a region-of-interest (ROI), and form a monochromatic image of the projection CT data at the optimized energy using the two or more basis material projections.

According to another aspect of the present invention, a method of diagnostic imaging includes acquiring projections of energy sensitive CT data and classifying the acquired projections into one of a first energy bin and a second energy bin. The method further includes decomposing the first and second energy bins into projection CT data of at least two basis materials, calculating an optimized linear attenuation coefficient based on the at least two basis materials, and generating an optimized monochromatic image using the optimized linear attenuation coefficient obtained from a weighed sum of projection CT data of the at least two basis materials.

According to yet another aspect of the present invention, a computer readable storage medium includes instructions stored thereon that, when executed by a processor, causes the computer to acquire x-ray projection data of energy sensitive CT data, classify the projection data into one of a first energy bin and a second energy bin, and decompose the first and second energy bins into projection CT data of two or more basis materials. The instructions further cause the computer to calculate an optimized virtual energy for the two or more basis materials, and generate an optimized monochromatic image at the optimized virtual energy using a weighted sum of the projection CT data of the two or more basis materials.

Various other features and advantages of the present invention will be made apparent from the following detailed description and the drawings.

BRIEF DESCRIPTION OF THE DRAWINGS

The drawings illustrate one preferred embodiment presently contemplated for carrying out the invention.

In the drawings.

DETAILED DESCRIPTION OF THE PREFERRED EMBODIMENT

Diagnostics devices comprise x-ray systems, magnetic resonance (MR) systems, ultrasound systems, computed tomography (CT) systems, positron emission tomography (PET) systems, ultrasound, nuclear medicine, and other types of imaging systems. Applications of x-ray sources comprise imaging, medical, security, and industrial inspection applications. However, it will be appreciated by those skilled in the art that an implementation is applicable for use with single-slice or other multi-slice configurations. Moreover, an implementation is employable for the detection and conversion of x-rays. However, one skilled in the art will further appreciate that an implementation is employable for the detection and conversion of other high frequency electromagnetic energy. An implementation is employable with a "third generation" CT scanner and/or other CT systems.

The operating environment of the present invention is described with respect to a sixty-four-slice computed tomography (CT) system. However, it will be appreciated by those skilled in the art that the present invention is equally applicable for use with other multi-slice configurations. Moreover, the present invention will be described with respect to the detection and conversion of x-rays. However, one skilled in the art will further appreciate that the present invention is equally applicable for the detection and conversion of other high frequency electromagnetic energy. The present invention will be described with respect to a "third generation" CT scanner, but is equally applicable with other CT systems.

Figure 1:
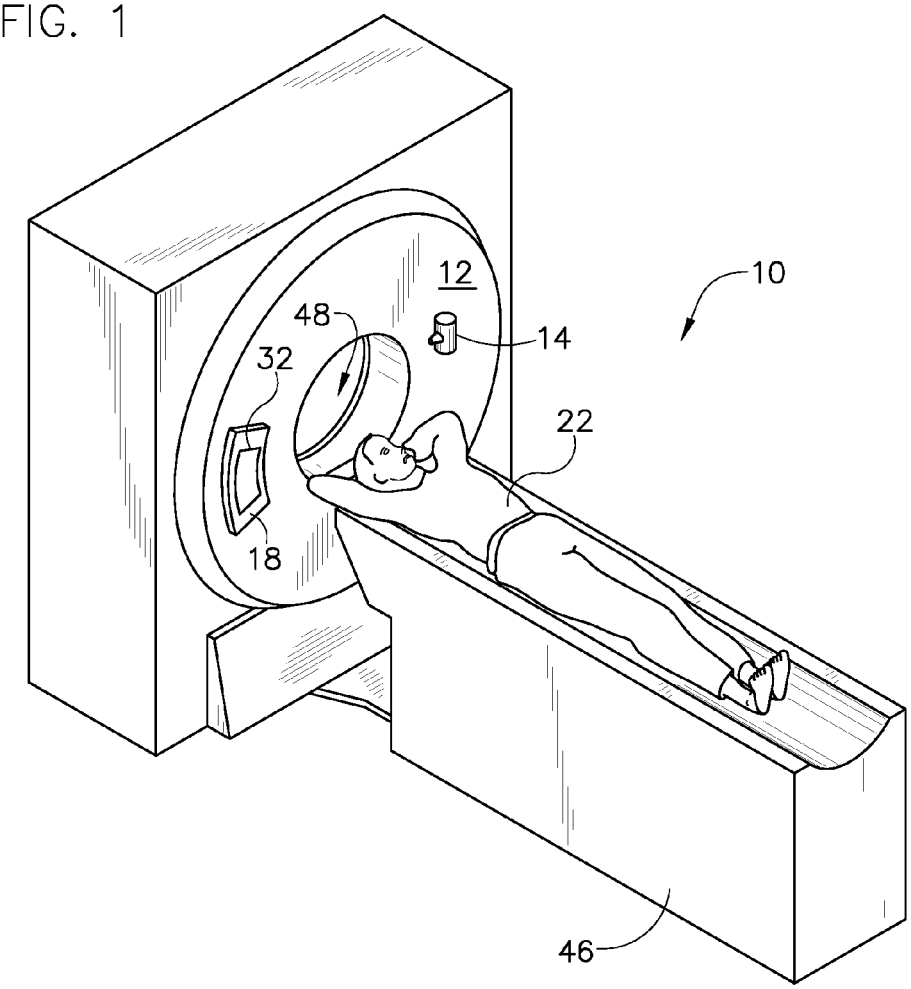
FIG. 1 is a pictorial view of a CT imaging system.
Figure 2:
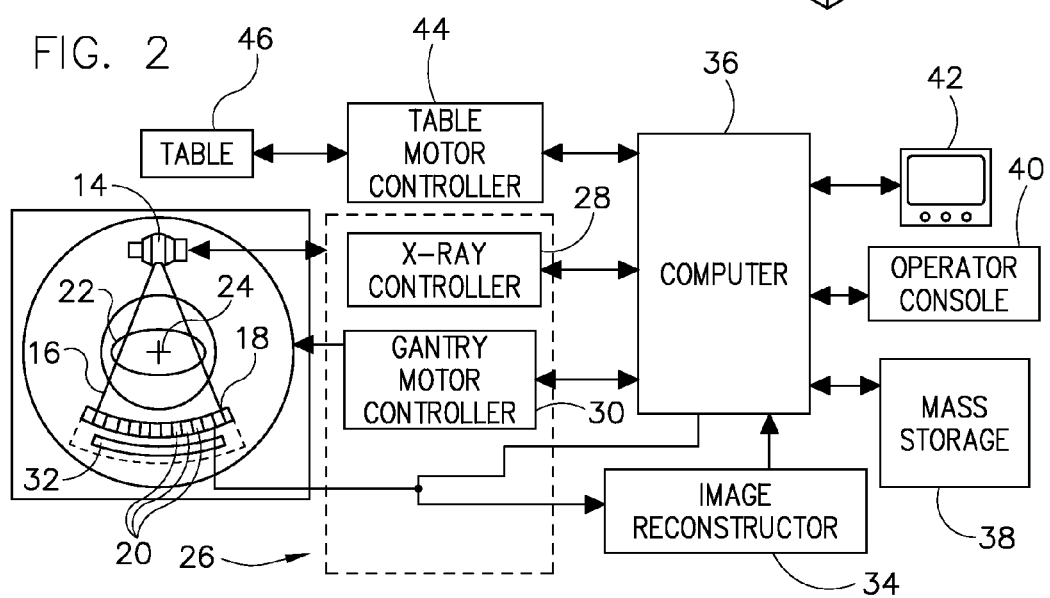
FIG. 2 is a block schematic diagram of the system illustrated in FIG. 1.

Referring to FIG. 1, a computed tomography (CT) imaging system 10 is shown as including a gantry 12 representative of a "third generation" CT scanner. Gantry 12 has an x-ray source 14 that projects a beam of x-rays 16 toward a detector assembly or collimator 18 on the opposite side of the gantry 12. Referring now to FIG. 2, detector assembly 18 is formed by a plurality of detectors 20 and data acquisition systems (DAS) 32. The plurality of detectors 20 sense the projected x-rays that pass through a medical patient 22, and DAS 32 converts the data to digital signals for subsequent processing. Each detector 20 produces an analog electrical signal that represents the intensity of an impinging x-ray beam and hence the attenuated beam as it passes through the patient 22. During a scan to acquire x-ray projection data, gantry 12 and the components mounted thereon rotate about a center of rotation 24.

Rotation of gantry 12 and the operation of x-ray source 14 are governed by a control mechanism 26 of CT system 10. Control mechanism 26 includes an x-ray controller 28 that provides power and timing signals to an x-ray source 14 and a gantry motor controller 30 that controls the rotational speed and position of gantry 12. An image reconstructor 34 receives sampled and digitized x-ray data from DAS 32 and performs high speed reconstruction. The reconstructed image is applied as an input to a computer 36 which stores the image in a mass storage device 38.

Computer 36 also receives commands and scanning parameters from an operator via console 40 that has some form of operator interface, such as a keyboard, mouse, voice activated controller, or any other suitable input apparatus. An associated display 42 allows the operator to observe the reconstructed image and other data from computer 36. The operator supplied commands and parameters are used by computer 36 to provide control signals and information to DAS 32, x-ray controller 28 and gantry motor controller 30. In addition, computer 36 operates a table motor controller 44 which controls a motorized table 46 to position patient 22 and gantry 12. Particularly, table 46 moves patients 22 through a gantry opening 48 of FIG. 1 in whole or in part.

Figure 3:
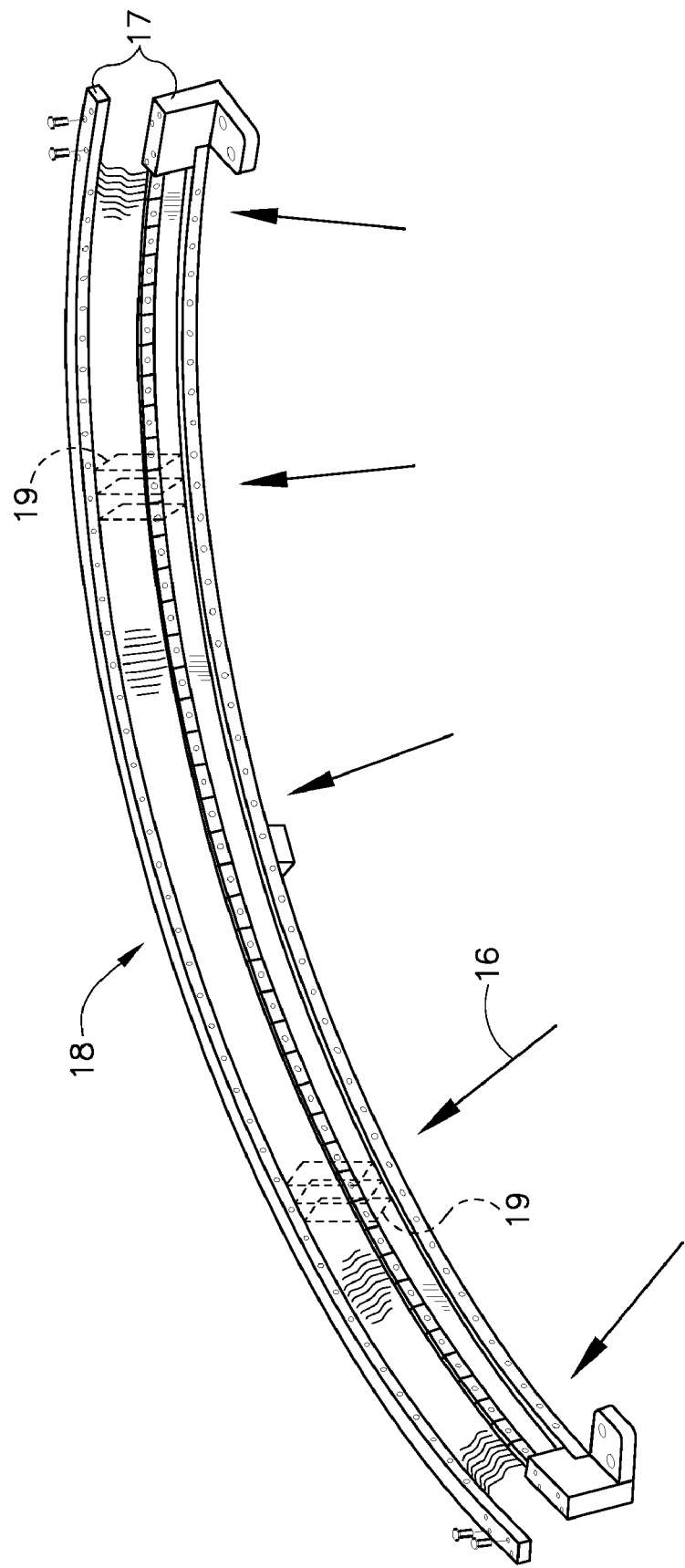
FIG. 3 is a perspective view of one embodiment of a CT system detector array.

As shown in FIG. 3, detector assembly 18 includes rails 17 having collimating blades or plates 19 placed therebetween. Plates 19 are positioned to collimate x-rays 16 before such beams impinge upon, for instance, detector 20 of FIG. 4 positioned on detector assembly 18. In one embodiment, detector assembly 18 includes 57 detectors 20, each detector 20 having an array size of 64×16 of pixel elements 50. As a result, detector assembly 18 has 64 rows and 912 columns (16×57 detectors) which allows 64 simultaneous slices of data to be collected with each rotation of gantry 12.

Figure 4:
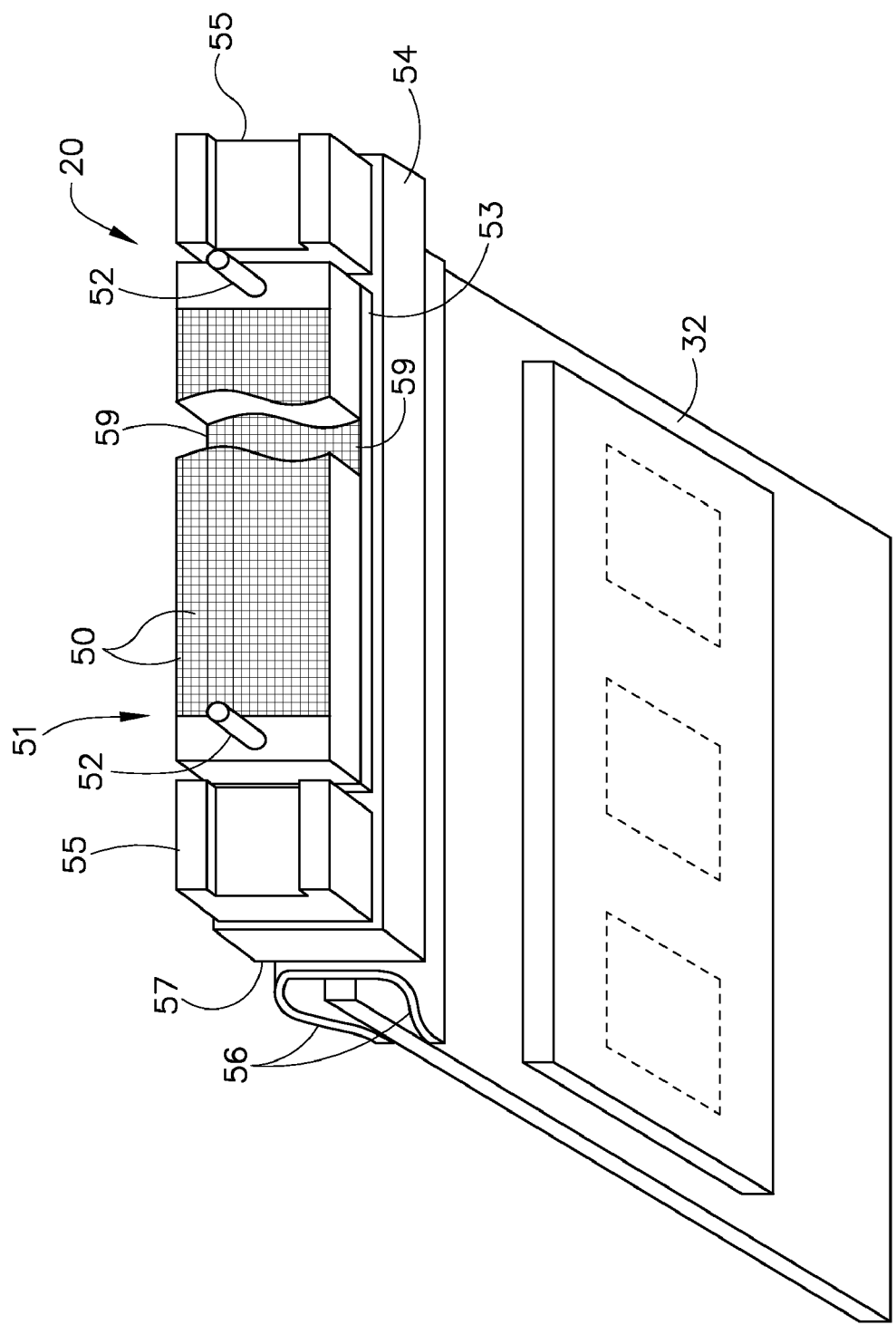
FIG. 4 is a perspective view of one embodiment of a CT detector.

Referring to FIG. 4, detector 20 includes DAS 32, with each detector 20 including a number of detector elements 50 arranged in pack 51. Detectors 20 include pins 52 positioned within pack 51 relative to detector elements 50. Pack 51 is positioned on a backlit diode array 53 having a plurality of diodes 59. Backlit diode array 53 is in turn positioned on multi-layer substrate 54. Spacers 55 are positioned on multi-layer substrate 54. Detector elements 50 are optically coupled to backlit diode array 53, and backlit diode array 53 is in turn electrically coupled to multi-layer substrate 54. Flex circuits 56 are attached to face 57 of multi-layer substrate 54 and to DAS 32. Detectors 20 are positioned within detector assembly 18 by use of pins 52.

In the operation of one embodiment, x-rays impinging within detector elements 50 generate photons which traverse pack 51, thereby generating an analog signal which is detected on a diode within backlit diode array 53. The analog signal generated is carried through multi-layer substrate 54, through flex circuits 56, to DAS 32 wherein the analog signal is converted to a digital signal.

As described above, each detector 20 may be designed to directly convert radiographic energy to electrical signals containing energy discriminatory or photon count data. In a preferred embodiment, each detector 20 includes a semiconductor layer fabricated from CZT. Each detector 20 also includes a plurality of metallized anodes attached to the semiconductor layer. As will be described, such detectors 20 may include an electrical circuit having multiple comparators thereon which may reduce statistical error due to pileup of multiple energy events.

Figure 5:
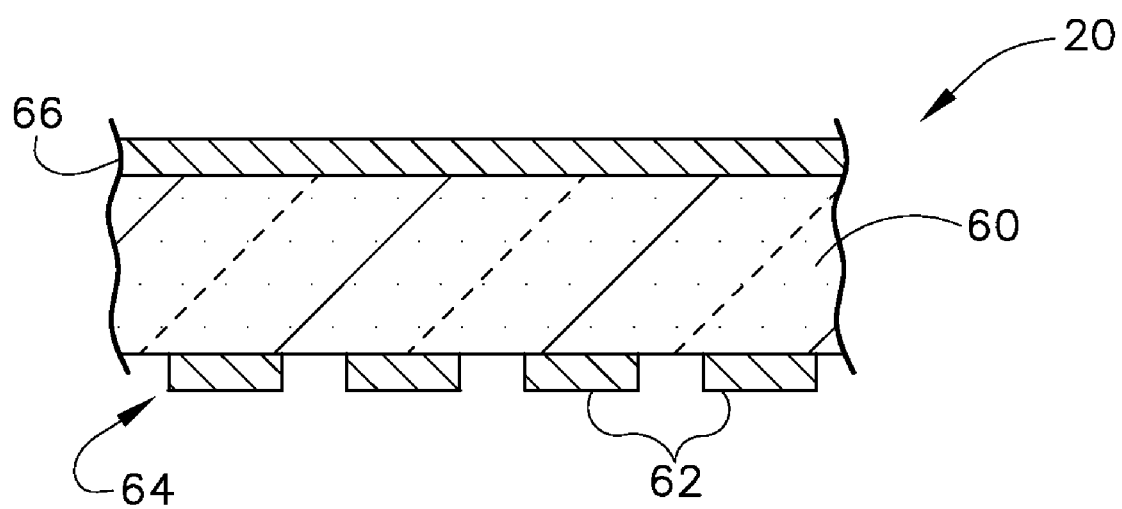
FIG. 5 is a cross-sectional view of one embodiment of a portion of a direct conversion detector.

Referring now to FIG. 5, a portion of a CZT or direct conversion detector in accordance with one embodiment of the present invention is shown. Detector 20 is defined by a semiconductor layer 60 having a number of electronically pixelated structures or pixels to define a number of detector elements, anodes, or contacts 62. This electronic pixelation is accomplished by applying a 2D array 64 of electrical contacts 62 onto a layer 60 of direct conversion material.

Detector 20 includes a contiguous high-voltage electrode 66 attached to semiconductor layer 60. The high-voltage electrode 66 is connected to a power supply (not shown) and it is designed to power the semiconductor layer 60 during the x-ray detection process. One skilled in the art will appreciate that the high-voltage layer 66 should be relatively thin so as to reduce the x-ray absorption characteristics and, in a preferred embodiment, is a few hundred angstroms in thickness. In a preferred embodiment, the high-voltage electrode 66 may be affixed to the semiconductor layer 60 through a metallization process. X-ray photons that impinge upon the semiconductor layer 60 will generate an electrical charge therein, which is collected in one or more of the electrical contacts 62, and which may be read out to the DAS 32 of FIG. 2. The amplitude of the charge collected is indicative of the energy of the photon that created the charge.

Referring back to FIGS. 1 and 2, an illustrative discussion is now presented in connection with an exemplary implementation of a decomposition algorithm. An image or slice is computed which may incorporate, in certain modes, less or more than 360 degrees of projection data to formulate an image. The image may be collimated to desired dimensions using tungsten blades in front of the x-ray source and different detector apertures. A collimator typically defines the size and shape of the beam of x-rays 16 that emerges from the x-ray source 14, and a bowtie filter may be included in the system 10 to further control the dose to the patient 22. A typical bowtie filter attenuates the beam of x-rays 16 to accommodate the body part being imaged, such as head or torso, such that, in general, less attenuation is provided for x-rays passing through or near an isocenter of the patient 22. The bowtie filter shapes the x-ray intensity during imaging in accordance with the region-of-interest (ROI), field of view (FOV), and/or target region of the patient 22 being imaged.

As the x-ray source 14 and the detector array 18 rotate, the detector array 18 collects data of the attenuated x-ray beams. The data collected by the detector array 18 undergoes pre-processing and calibration to condition the data to represent the line integrals of the attenuation coefficients of the scanned object or the patient 22. The processed data are commonly called projections.

In EDCT/MECT/DE-CT, two or more sets of projection data are typically obtained for the imaged object at different tube peak kilovoltage (kVp) levels, which change the peak and spectrum of energy of the incident photons comprising the emitted x-ray beams or, alternatively, at a single tube peak kilovoltage (kVp) level or spectrum with an energy resolving detector of the detector array 18. The acquired sets of projection data may be used for basis material decomposition (BMD). During BMD, the measured projections are converted to a set of density line-integral projections. The density line-integral projections may be reconstructed to form a density map or image of each respective basis material, such as bone, soft tissue, and/or contrast agent maps. The density maps or images may be, in turn, associated to form a volume rendering of the basis material, for example, bone, soft tissue, and/or contrast agent, in the imaged volume.

Once reconstructed, the basis material image produced by the CT system 10 reveals internal features of the patient 22, expressed in the densities of the two basis materials. The density image may be displayed to show these features. In traditional approaches to diagnosis of medical conditions, such as disease states, and more generally of medical events, a radiologist or physician would consider a hard copy or display of the density image to discern characteristic features of interest. Such features might include lesions, sizes and shapes of particular anatomies or organs, and other features that would be discernable in the image based upon the skill and knowledge of the individual practitioner.

In addition to a CT number or Hounsfield value, an energy selective CT system can provide additional information related to a material's atomic number and density. This information may be particularly useful for a number of medical clinical applications, where the CT number of different materials may be similar but the atomic number may be quite different. For example, calcified plaque and iodine-contrast enhanced blood may be located together in coronary arteries or other vessels. As will be appreciated by those skilled in the art, calcified plaque and iodine-contrast enhanced blood are known to have distinctly different atomic numbers, but at certain densities these two materials are indistinguishable by CT number alone.

A decomposition algorithm is employable to generate atomic number and density information from energy sensitive x-ray measurements. Multiple energy techniques comprise dual energy, photon counting energy discrimination, dual layered scintillation and/or one or more other techniques designed to measure x-ray attenuation in two or more distinct energy ranges. As an example, any compound or mixture of materials measured with a multiple energy technique may be represented as a hypothetical material having the same x-ray energy attenuation characteristics. This hypothetical material can be assigned an effective atomic number Z. Unlike the atomic number of an element, effective atomic number of a compound is defined by the x-ray attenuation characteristics, and it need not be an integer. This effective Z representation property stems from a well-known fact that x-ray attenuation in the energy range useful for diagnostic x-ray imaging is strongly related to the electron density of compounds, which is also related to the atomic number of materials.

Figure 6:
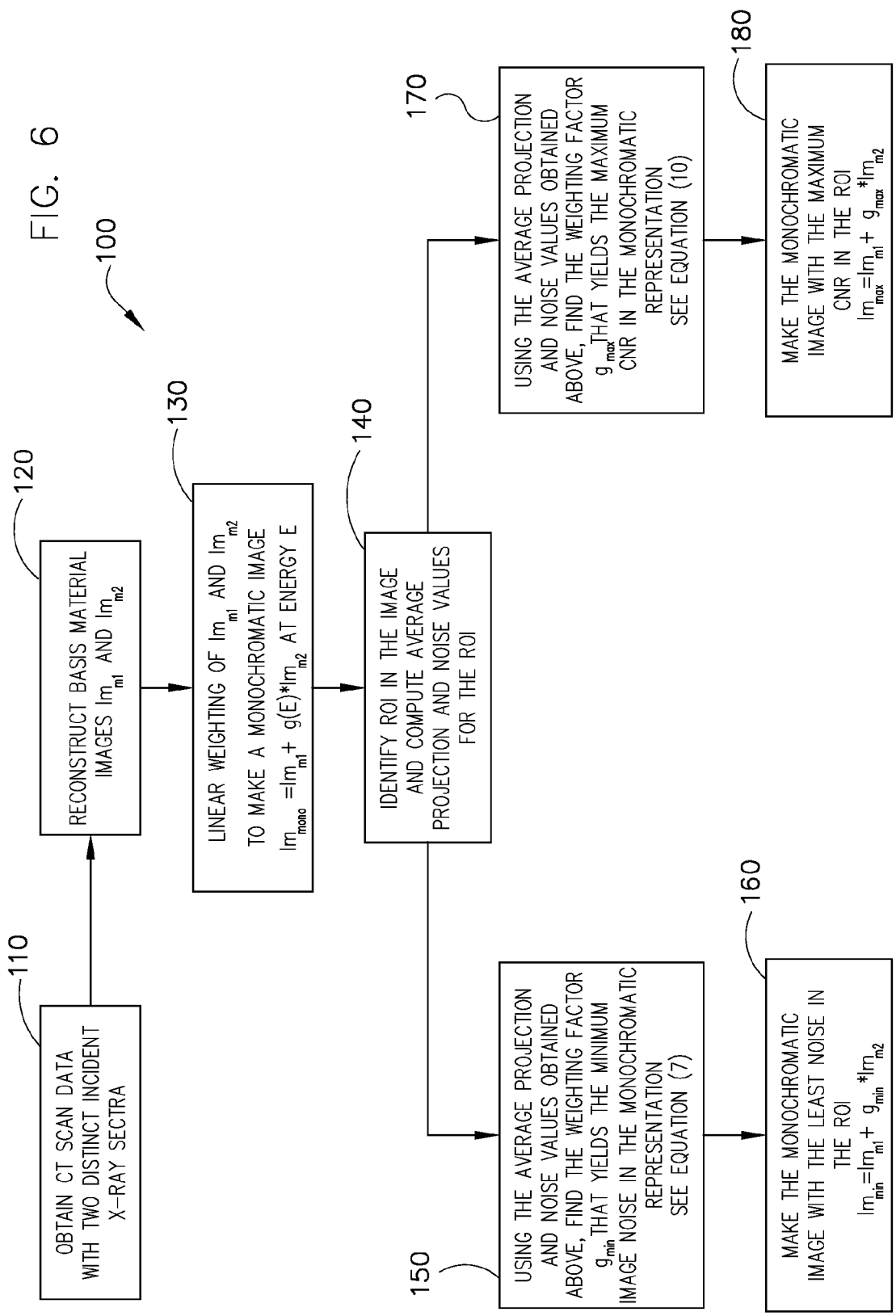
FIG. 6 is a block schematic diagram of a technique to determine an optimized image according to an embodiment of the present invention.

In an example of the present invention, BMD images may be reformatted to produce a new image with x-ray attenuation coefficients equivalent to a chosen monochromatic energy. Referring now to FIG. 6, a technique 100 describes steps that may determine an optimized monochromatic energy by either minimizing the noise in an ROI or by maximizing a contrast-to-noise ratio (CNR) in an ROI. In STEP 110, energy discriminatory CT data is obtained having at least two distinct incident energy spectra. In STEP 120, basis material images $Im_{m1}$, $Im_{m2}$ are reconstructed, and in STEP 130, a linear weighting coefficient g(E) is used to make a monochromatic image $Im_{mono}$ as a function of g(E). $Im_{mono}$ may be optimized by either minimizing the monochromatic noise in the image, or by maximizing the CNR and is defined generically by the equation:

$$Im_{mono} = Im_{m1} + g(E) * Im_{m2} \quad \text{(Eqn. 1)},$$

where g(E) is an energy dependent weighting factor.

At STEP 140, an ROI within the image is identified, and average projection and noise values are computed for the identified ROI. Let:

$p_1$, $p_2$=normalized and negatively logged projection pairs obtained at the same ray path, respectively with two different incident x-ray spectra;

$p_{m1}$, $p_{m2}$=projection pairs corresponding to the density line integration of two basis materials, $m_1$ and $m_2$;

$f_1(p_1, p_2)$, $f_2(p_1, p_2)$=material decomposition functions for basis material m1 and m2;

$p_{mono}$=projection value of x-ray attenuation at a given monochromatic energy E; and $\mu_{m1}(E)$, $\mu_{m2}(E)$=attenuation coefficients of the two basis materials at energy E.

Using the basis material decomposition, the decomposed projection values correspond to the integrated density of material m1 and m2 are expressed as $p_{m1} = f_1(p_1, p_2)$, and $p_{m2} = f_2(p_1, p_2)$. The corresponding monochromatic projection at energy E can be computed as $$p_{mono} = \mu_{m1}(E)p_{m1} + \mu_{m2}(E)p_{m2} = \mu_{m1}(E)f_1(p_1,p_2) + \mu_{m2}(E)f_2(p_1,p_2) \quad \text{Eqn. 2)}.$$

Equation 2 can be normalized to have one weighting parameter g(E) for functions $f_1(p_1, p_2)$, $f_2(p_1, p_2)$ by dropping one scaling parameter, thus $$p_{mono} = f_1(p_1, p_2) + \frac{\mu_{m2}(E)}{\mu_{m1}(E)} f_2(p_1, p_2) \quad \text{(Eqn. 3)}$$
$$= f_1(p_1, p_2) + g(E)f_2(p_1, p_2),$$

where, $g(E) = \frac{\mu_{m2}(E)}{\mu_{m1}(E)}$.

According to an embodiment of the present invention, at STEP 150, a weighting factor $g_{min}$ is computed and substituted into Eqn. 1 to obtain a minimized monochromatic noise, thus determining a minimized monochromatic noise image $Im_{min}$. According to this embodiment, $g_{min}$ is obtained in the following fashion.

The monochromatic image noise can be computed using Eqn. (3) and the associated noise in measured projections $p_1$ and $p_2$, by accounting for all the projection angles and the image reconstruction process. However, to find the proper g(E) value with which the monochromatic image fully cancels the natively correlated noise generated by the material decomposition functions $f_1(p_1, p_2)$ and $f_2(p_1, p_2)$, the condition for which g(E) yields the minimum noise in the image can be simplified and well-approximated with the following approach. Let:

$\bar{p}_1$, $\bar{p}_2$=projection pairs obtained with two different incident x-ray spectra, by averaging all the projections that contribute to a region of interest (ROI) in the image;

$\bar{\Delta}_1$, $\bar{\Delta}_2$=noise values associated with projections $\bar{p}_1$, $\bar{p}_2$;

$\bar{p}_{mono}$=associated monochromatic projection value at energy E; and $g_{min}$=weighting at which the monochromatic image has the minimum noise.

With the definitions above, equation (3) can be approximated as, $$\bar{p}_{mono} = f_1(\bar{p}_1, \bar{p}_2) + g(E)f_2(\bar{p}_1, \bar{p}_2) \quad \text{(Eqn. 4)}.$$

Noise $\bar{\Delta}_1$ and $\bar{\Delta}_2$ are typically independent, thus, the resultant variance of the monochromatic projection $\bar{p}_{mono}$ can be computed as $$(\bar{\Delta}_{mono})^2 = \left(\frac{\partial(f_1(\bar{p}_1, \bar{p}_2) + g(E)f_2(\bar{p}_1, \bar{p}_2))}{\partial \bar{p}_1}\right)^2 \bar{\Delta}_1^2 + \quad \text{(Eqn. 5)}$$
$$\left(\frac{\partial(f_1(\bar{p}_1, \bar{p}_2) + g(E)f_2(\bar{p}_1, \bar{p}_2))}{\partial \bar{p}_2}\right)^2 \bar{\Delta}_2^2.$$

The minimum noise within the ROI that yields the average projection values ($\bar{p}_1$, $\bar{p}_2$) can be obtained as $$\frac{\partial(\bar{\Delta}_{mono})^2}{\partial g} = 0.$$

That is, $$\left(\frac{\partial(f_1(\bar{p}_1, \bar{p}_2) + g_{min}f_2(\bar{p}_1, \bar{p}_2))}{\partial \bar{p}_1}\right)\frac{\partial f_2(\bar{p}_1, \bar{p}_2)}{\partial \bar{p}_1}\bar{\Delta}_1^2 + \quad \text{(Eqn. 6)}$$
$$\left(\frac{\partial(f_1(\bar{p}_1, \bar{p}_2) + g_{min}f_2(\bar{p}_1, \bar{p}_2))}{\partial \bar{p}_2}\right)\frac{\partial f_2(\bar{p}_1, \bar{p}_2)}{\partial \bar{p}_2}\bar{\Delta}_2^2 = 0.$$

Thus, the best weighting for minimum noise in the monochromatic image is when, $$g_{min} = -\frac{\frac{\partial f_1(\bar{p}_1, \bar{p}_2)}{\partial \bar{p}_1}\frac{\partial f_2(\bar{p}_1, \bar{p}_2)}{\partial \bar{p}_1}\bar{\Delta}_1^2 + \frac{\partial f_1(\bar{p}_1, \bar{p}_2)}{\partial \bar{p}_2}\frac{\partial f_2(\bar{p}_1, \bar{p}_2)}{\partial \bar{p}_2}\bar{\Delta}_2^2}{\left(\frac{\partial f_2(\bar{p}_1, \bar{p}_2)}{\partial \bar{p}_1}\right)^2\bar{\Delta}_1^2 + \left(\frac{\partial f_2(\bar{p}_1, \bar{p}_2)}{\partial \bar{p}_2}\right)^2\bar{\Delta}_2^2}.$$

(Eqn. 7)

The corresponding x-ray energy at which the monochromatic image has the least noise value is, $E=g^{-1}(g_{min})$. Accordingly, at STEP 160, an optimized image with minimized monochromatic noise $Im_{min}$ is obtained by substituting $g_{min}$ into generic Eqn. 1, thus $Im_{min}=Im_{m1}+g_{min}Im_{m2}$.

Referring still to FIG. 6, according to an alternate embodiment of the present invention, at STEP 170, a weighting factor $g_{max}$ is computed and substituted into Eqn. 1 to obtain a maximized CNR, thus determining a maximized monochromatic noise image $Im_{max}$. According to this embodiment, $g_{max}$ is obtained in the following fashion.

Assuming the material $m_2$ is the target contrast, $$(CNR)^2 = K\frac{g(E)^2}{\left(\frac{\partial (f_1(\bar{p}_1, \bar{p}_2)+g(E)f_2(\bar{p}_1, \bar{p}_2))}{\partial \bar{p}_1}\right)^2\bar{\Delta}_1^2 + \left(\frac{\partial (f_1(\bar{p}_1, \bar{p}_2)+g(E)f_2(\bar{p}_1, \bar{p}_2))}{\partial \bar{p}_2}\right)^2\bar{\Delta}_2^2}$$

(Eqn. 8)

where K is a constant. The condition for maximum CNR is $$\frac{\partial\left\{\frac{g_{max}^2}{\left(\frac{\partial (f_1(\bar{p}_1, \bar{p}_2)+g_{max}f_2(\bar{p}_1, \bar{p}_2))}{\partial \bar{p}_1}\right)^2\bar{\Delta}_1^2 + \left(\frac{\partial (f_1(\bar{p}_1, \bar{p}_2)+g_{max}f_2(\bar{p}_1, \bar{p}_2))}{\partial \bar{p}_2}\right)^2\bar{\Delta}_2^2}\right\}}{\partial g_{max}} = 0,.$$

(Eqn. 9)

By solving equation (9), weight factor $g_{max}$ can be obtained, with the corresponding energy $E=g^{-1}(g_{max})$.

$$\text{Thus, } g_{max} = \sqrt{\frac{\left(\frac{\partial f_1(p_1, p_2)}{\partial p_1}\right)^2\Delta_1^2 + \left(\frac{\partial f_1(p_1, p_2)}{\partial \bar{p}_2}\right)^2\Delta_2^2}{\left(\frac{\partial f_2(\bar{p}_1, p_2)}{\partial p_1}\right)^2\Delta_1^2 + \left(\frac{\partial f_2(\bar{p}_1, p_2)}{\partial p_2}\right)^2\Delta_2^2}}.$$

(Eqn. 10)

Accordingly, at STEP 180, an optimized image with maximized CNR $Im_{max}$ is obtained by substituting $g_{max}$ into generic Eqn. 1, thus $Im_{max}=Im_{m1}+g_{max}Im_{m2}$.

Figure 7:
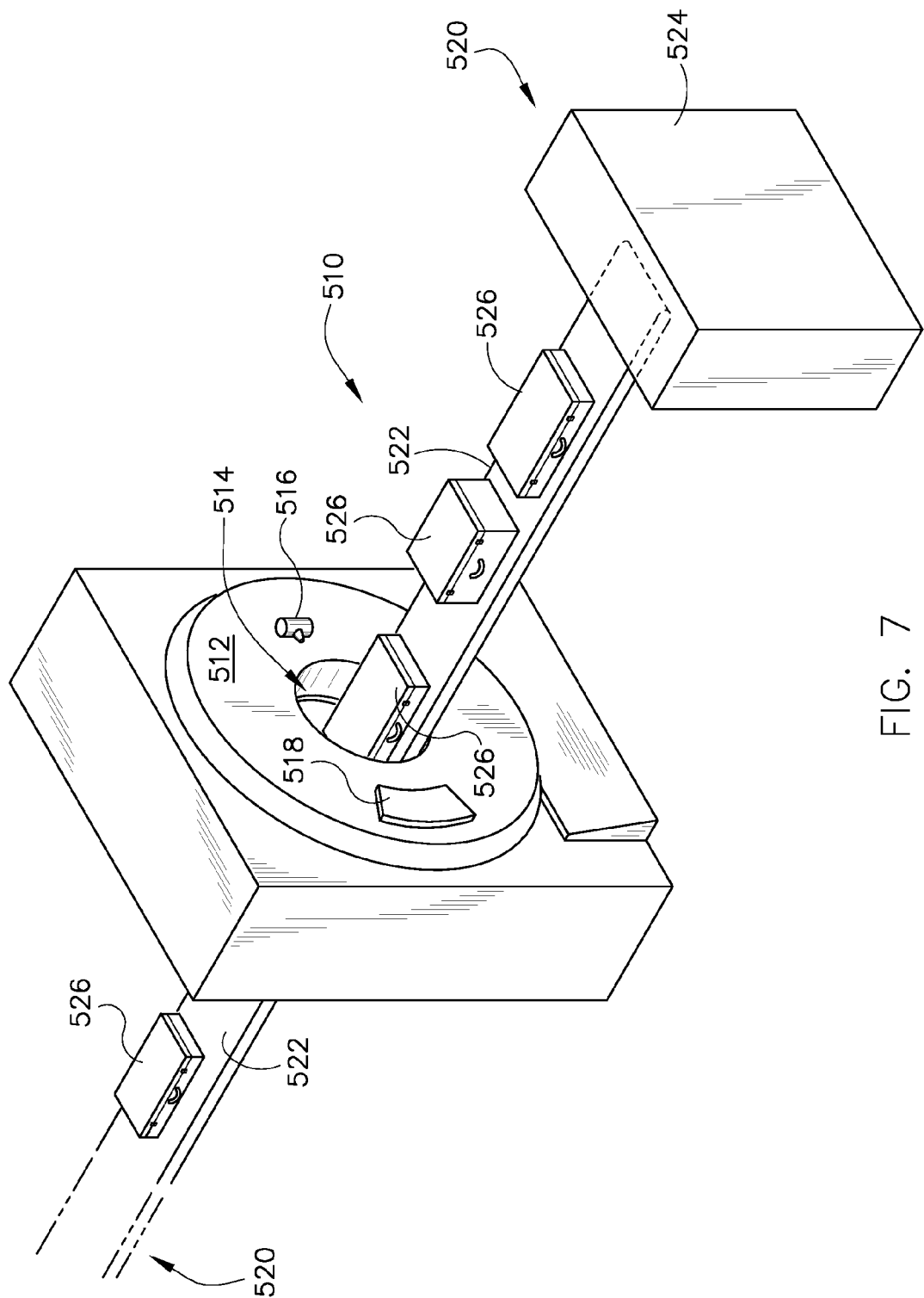
FIG. 7 is a pictorial view of a CT system for use with a non-invasive package inspection system.

Referring now to FIG. 7, package/baggage inspection system 510 includes a rotatable gantry 512 having an opening 514 therein through which packages or pieces of baggage may pass. The rotatable gantry 512 houses an x-ray and/or high frequency electromagnetic energy source 516 as well as a detector assembly 518 having scintillator arrays comprised of scintillator cells. A conveyor system 520 is also provided and includes a conveyor belt 522 supported by structure 524 to automatically and continuously pass packages or baggage pieces 526 through opening 514 to be scanned. Objects 526 are fed through opening 514 by conveyor belt 522, imaging data is then acquired, and the conveyor belt 522 removes the packages 526 from opening 514 in a controlled and continuous manner. As a result, postal inspectors, baggage handlers, and other security personnel may non-invasively inspect the contents of packages 526 for explosives, knives, guns, contraband, etc. An exemplary implementation can aid in the development of automatic inspection techniques, such as explosive detection in luggage.

An implementation of the system 10 and/or 510 in an example comprises a plurality of components such as one or more of electronic components, hardware components, and/or computer software components. A number of such components can be combined or divided in an implementation of the system 10 and/or 510. An exemplary component of an implementation of the system 10 and/or 510 employs and/or comprises a set and/or series of computer instructions written in or implemented with any of a number of programming languages, as will be appreciated by those skilled in the art. An implementation of the system 10 and/or 510 in an example comprises any (e.g., horizontal, oblique, or vertical) orientation, with the description and figures herein illustrating an exemplary orientation of an implementation of the system 10 and/or 510, for explanatory purposes.

An implementation of the system 10 and/or the system 510 in an example employs one or more computer readable signal bearing media. A computer-readable signal-bearing medium in an example stores software, firmware and/or assembly language for performing one or more portions of one or more implementations. An example of a computer-readable signal bearing medium for an implementation of the system 10 and/or the system 510 comprises the recordable data storage medium of the image reconstructor 34, and/or the mass storage device 38 of the computer 36. A computer-readable signal-bearing medium for an implementation of the system 10 and/or the system 510 in an example comprises one or more of a magnetic, electrical, optical, biological, and/or atomic data storage medium. For example, an implementation of the computer-readable signal-bearing medium comprises floppy disks, magnetic tapes, CD-ROMs, DVD-ROMs, hard disk drives, and/or electronic memory. In another example, an implementation of the computer-readable signal-bearing medium comprises a modulated carrier signal transmitted over a network comprising or coupled with an implementation of the system 10 and/or the system 510, for instance, one or more of a telephone network, a local area network ("LAN"), a wide area network ("WAN"), the Internet, and/or a wireless network.

Therefore, according to an embodiment of the present invention, a diagnostic imaging system includes a high frequency electromagnetic energy source that emits a beam of high frequency electromagnetic energy toward an object to be imaged, a detector that receives high frequency electromagnetic energy emitted by the high frequency electromagnetic energy source and attenuated by the object, a data acquisition system (DAS) operably connected to the detector, and a computer operably connected to the DAS. The computer is programmed to obtain CT scan data with two or more incident energy spectra, decompose the obtained CT scan data into projection CT data of two or more basis materials, reconstruct linearly weighted projections of the two or more basis materials, determine an optimized energy for the two or more basis materials within a region-of-interest (ROI), and form a monochromatic image of the projection CT data at the optimized energy using the two or more basis material projections.

According to another embodiment of the present invention, a method of diagnostic imaging includes acquiring projections of energy sensitive CT data and classifying the acquired projections into one of a first energy bin and a second energy bin. The method further includes decomposing the first and second energy bins into projection CT data of at least two basis materials, calculating an optimized linear attenuation coefficient based on the at least two basis materials, and generating an optimized monochromatic image using the optimized linear attenuation coefficient obtained from a weighed sum of projection CT data of the at least two basis materials.

According to yet another embodiment of the present invention, a computer readable storage medium includes instructions stored thereon that, when executed by a processor, causes the computer to acquire x-ray projection data of energy sensitive CT data, classify the projection data into one of a first energy bin and a second energy bin, and decompose the first and second energy bins into projection CT data of two or more basis materials. The instructions further cause the computer to calculate an optimized virtual energy for the two or more basis materials, and generate an optimized monochromatic image at the optimized virtual energy using a weighted sum of the projection CT data of the two or more basis materials.

The present invention has been described in terms of the preferred embodiment, and it is recognized that equivalents, alternatives, and modifications, aside from those expressly stated, are possible and within the scope of the appending claims.

What is claimed is:

1. A diagnostic imaging system comprising:
   a high frequency electromagnetic energy source that emits a beam of high frequency electromagnetic energy toward an object to be imaged;
   a detector that receives high frequency electromagnetic energy emitted by the high frequency electromagnetic energy source and attenuated by the object;
   a data acquisition system (DAS) operably connected to the detector; and
   a computer operably connected to the DAS and programmed to:
      obtain CT scan data with two or more incident energy spectra;
      decompose the obtained CT scan data into projection CT data of two or more basis materials;
      reconstruct linearly weighted projections of the two or more basis materials;
      determine an optimized energy for the two or more basis materials within a region-of-interest (ROI); and
      form a monochromatic image of the projection CT data at the optimized energy using the two or more basis material projections.

2. The diagnostic imaging system of claim 1 wherein the monochromatic image ($\text{Im}_{min}$) is formed at the optimized energy that has a minimized noise in the ROI.

3. The diagnostic imaging system of claim 2 wherein $\text{Im}_{min} = \text{Im}_{m1} g_{min} \text{Im}_{m2}$, and wherein $\text{Im}_{m1}$, $\text{Im}_{m2}$ are reconstructed images representing densities of basis materials, and $g_{min}$ is a weighting factor at which the monochromatic image has the minimized noise.

4. The diagnostic imaging system of claim 3 wherein a monochromatic projection $p_{mono}$ at energy E is estimated with the equation $\bar{p}_{mono} = f_1(\bar{p}_1, \bar{p}_2) + g(E) f_2(\bar{p}_1, \bar{p}_2)$, and $\bar{p}1, \bar{p}2$ represent average projection pairs obtained with two different incident x-ray spectra, and the minimized noise within the ROI that yields the average projection values $\bar{p}_1, \bar{p}_2$ are obtained by setting $$\frac{\partial (\bar{\Delta}_{mono})^2}{\partial g} = 0; \text{ wherein}$$

$$(\bar{\Delta}_{mono})^2 = \left(\frac{\partial (f_1(\bar{p}_1, \bar{p}_2) + g(E) f_2(\bar{p}_1, \bar{p}_2))}{\partial \bar{p}_1}\right)^2 \bar{\Delta}_1^2 + \left(\frac{\partial (f_1(\bar{p}_1, \bar{p}_2) + g(E) f_2(\bar{p}_1, \bar{p}_2))}{\partial \bar{p}_2}\right)^2 \bar{\Delta}_2^2,$$

$\bar{\Delta}_1, \bar{\Delta}_2$ are noise values associated with projection values $\bar{p}_1, \bar{p}_2$, and the x-ray energy at which the monochromatic image noise is minimized is $E = g^{-1}(g_{min})$; thus $$g_{min} = -\frac{\frac{\partial f_1(\bar{p}_1, \bar{p}_2)}{\partial \bar{p}_1} \frac{\partial f_2(\bar{p}_1, \bar{p}_2)}{\partial \bar{p}_1} \bar{\Delta}_1^2 + \frac{\partial f_1(\bar{p}_1, \bar{p}_2)}{\partial \bar{p}_2} \frac{\partial f_2(\bar{p}_1, \bar{p}_2)}{\partial \bar{p}_2} \bar{\Delta}_2^2}{\left(\frac{\partial f_2(\bar{p}_1, \bar{p}_2)}{\partial \bar{p}_1}\right)^2 \bar{\Delta}_1^2 + \left(\frac{\partial f_2(\bar{p}_1, \bar{p}_2)}{\partial \bar{p}_2}\right)^2 \bar{\Delta}_2^2}.$$

5. The diagnostic imaging system of claim 1 wherein the monochromatic image ($\text{Im}_{max}$) is formed at an optimized energy that has a maximized contrast-to-noise ratio (CNR) in the ROI.

6. The diagnostic imaging system of claim 5 wherein $\text{Im}_{max} = \text{Im}_{m1} + g_{max} \text{Im}_{m2}$, and wherein $\text{Im}_{m1}, \text{Im}_{m2}$ are reconstructed images representing densities of basis materials, and $g_{max}$ is a weighting factor at which the CNR is maximized.

7. The diagnostic imaging system of claim 6 wherein a monochromatic projection $p_{CNR}$ at energy E is estimated with the equation $\bar{p}_{CNR} = \theta_1(\bar{p}_1, \bar{p}_2) + g(E) f_2(\bar{p}_1, \bar{p}_2)$, and $\bar{p}_1, \bar{p}_2$ represent average projection pairs obtained with two different incident x-ray spectra, and the maximum CNR within the ROI that yields the average projection values $\bar{p}_1, \bar{p}_2$ are obtained by setting $$\frac{\partial (CNR)^2}{\partial g} = 0; \text{ wherein}$$

$$(CNR)^2 = K \frac{g(E)^2}{\left(\frac{\partial (f_1(\bar{p}_1, \bar{p}_2) + g(E) f_2(\bar{p}_1, \bar{p}_2))}{\partial \bar{p}_1}\right)^2 \bar{\Delta}_1^2 + \left(\frac{\partial (f_1(\bar{p}_1, \bar{p}_2) + g(E) f_2(\bar{p}_1, \bar{p}_2))}{\partial \bar{p}_2}\right)^2 \bar{\Delta}_2^2}$$

$\bar{\Delta}_1, \bar{\Delta}_2$ are noise values associated with projection values $\bar{p}_1, \bar{p}_2$, K is a constant, and the x-ray energy at which the CNR is maximized is $E = g^{-1}(g_{max})$; and wherein the condition for obtaining $g_{max}$ at maximum CNR is:

$$\frac{\partial \left\{ \frac{g_{max}^2}{\left(\frac{\partial (f_1(\bar{p}_1, \bar{p}_2) + g_{max} f_2(\bar{p}_1, \bar{p}_2))}{\partial \bar{p}_1}\right)^2 \bar{\Delta}_1^2 + \left(\frac{\partial (f_1(\bar{p}_1, \bar{p}_2) + g_{max} f_2(\bar{p}_1, \bar{p}_2))}{\partial \bar{p}_2}\right)^2 \bar{\Delta}_2^2} \right\}}{\partial g_{max}} = 0,$$

-continued $$\text{thus } g_{max} = \sqrt{\frac{\left(\frac{\partial f_1(p_1, p_2)}{\partial p_1}\right)^2 \Delta_1^2 + \left(\frac{\partial f_1(p_1, p_2)}{\partial \overline{p}_2}\right)^2 \Delta_2^2}{\left(\frac{\partial f_2(p_1, p_2)}{\partial p_1}\right)^2 \Delta_1^2 + \left(\frac{\partial f_2(p_1, p_2)}{\partial p_2}\right)^2 \Delta_2^2}}.$$

8. The diagnostic imaging system of claim 1 wherein the detector comprises an EDCT detector that provides energy sensitive measurements of the high frequency electromagnetic energy emitted by the high frequency electromagnetic energy source.

9. The diagnostic imaging system of claim 1 wherein one of the two basis materials is water or iodine.

10. The diagnostic imaging system of claim 1 wherein the high frequency electromagnetic energy source is an x-ray tube.

11. A method of diagnostic imaging comprising:
acquiring projections of energy sensitive CT data;
classifying the acquired projections into one of a first energy bin and a second energy bin;
decomposing the first and second energy bins into projection CT data of at least two basis materials;
calculating an optimized linear attenuation coefficient based on the at least two basis materials; and
generating an optimized monochromatic image using the optimized linear attenuation coefficient obtained from a weighted sum of projection CT data of the at least two basis materials;
wherein the optimized linear attenuation coefficient is selected at an optimized energy that has the least noise in a region-of-interest (ROI).

12. The method of claim 11 wherein the at least two basis materials comprise at least one of iodine and water.

13. The method of claim 11 wherein the optimized linear attenuation coefficient is selected at an optimized energy that has a maximized contrast-to-noise ratio (CNR) in the ROI.

14. The method of claim 11 wherein the projections of energy sensitive CT data are acquired by an EDCT detector that provides energy sensitive measurements of high frequency electromagnetic energy emitted by a high frequency electromagnetic energy source.

15. A computer readable storage medium having stored thereon instructions that, when executed by a processor, cause a computer to:
acquire x-ray projection data of energy sensitive CT data;
classify the projection data into one of a first energy bin and a second energy bin;
decompose the first and second energy bins into projection CT data of two or more basis materials;
calculate an optimized virtual energy for the two or more basis materials; and
generate an optimized monochromatic image at the optimized virtual energy using a weighted sum of the projection CT data of the two or more basis materials;
wherein the instructions further cause the computer to select the optimized virtual energy at an energy that has a maximized contrast-to-noise ratio (CNR).

16. The computer readable storage medium of claim 15 wherein the two or more basis materials comprise at least one of iodine and water.

17. The computer readable storage medium of claim 15 wherein the instructions further cause the computer to select the optimized virtual energy at an energy that has minimized monochromatic noise.

18. The computer readable storage medium of claim 15 wherein the instructions that cause the computer to acquire x-ray projection data cause the computer to acquire x-ray projection data of the energy sensitive CT data by an EDCT detector that provides energy sensitive measurements of high frequency electromagnetic energy emitted by a high frequency electromagnetic energy source.

* * * * *

UNITED STATES PATENT AND TRADEMARK OFFICE
CERTIFICATE OF CORRECTION

PATENT NO. : 7,724,865 B2  Page 1 of 1
APPLICATION NO. : 11/843031
DATED : May 25, 2010
INVENTOR(S) : Wu et al.

It is certified that error appears in the above-identified patent and that said Letters Patent is hereby corrected as shown below:

On the Face Page, in the Figure, for Tag "110", in Line 3, delete "SECTRA" and insert -- SPECTRA --, therefor.

In Fig. 6, Sheet 5 of 6, for Tag "110", in Line 3, delete "SECTRA" and insert -- SPECTRA --, therefor.

In Column 7, Line 51, delete "m1 and m2;" and insert -- $m_1$ and $m_2$; --, therefor.

In Column 7, Line 59, delete "m1 and m2" and insert -- $m_1$ and $m_2$ --, therefor.

In Column 11, Line 60, in Claim 3, delete "$Im_{min}=Im_{m1}g_{min}Im_{m2}$," and insert -- $Im_{min}=Im_{m1}+g_{min}Im_{m2}$, --, therefor.

In Column 11, Line 66, in Claim 4, delete "$\overline{p1},\overline{p2}$" and insert -- $\overline{p}_1, \overline{p}_2$ --, therefor.

In Column 12, Line 37, in Claim 7, delete "$\overline{p}_{CNR}=f_1$" and insert -- $\overline{p}_{CNR}=f_1$ --, therefor.

Signed and Sealed this
Twenty-first Day of June, 2011

David J. Kappos
*Director of the United States Patent and Trademark Office*